United States Patent [19]
Higa et al.

[11] Patent Number: 4,755,529
[45] Date of Patent: Jul. 5, 1988

[54] GUAIAZULENE DERIVATIVES AND THEIR METHODS OF USE

[75] Inventors: Tatsuo Higa, Okinawa, Japan; Shinichi Sakemi, Vero Beach, Fla.

[73] Assignee: Harbor Branch Oceanographic Institution Inc., Ft. Pierce, Fla.

[21] Appl. No.: 879,080

[22] Filed: Jun. 26, 1986

[51] Int. Cl.$^4$ .................. A61K 31/34; C07D 307/93
[52] U.S. Cl. ................................. 514/468; 549/458
[58] Field of Search ..................... 549/458; 514/468

[56] References Cited

PUBLICATIONS

Takeda et al, Chem. Pharm. Bull., 1, pp. 164–169, (1953).
Fusetani et al, Experientia, 37, pp. 680–681, (1981).
Li et al, Tet. Letters, 25 (42), pp. 4707–4708, (1984).
Imre et al, Experientia, 37, pp. 442–443, (1981).
Li et al, Tet. Letters, 25 (6), pp. 587–590, (1984).
Takeda et al, J. Chem. Suc., pp. 2591–2597, (1964).
Chem. Abstracts, vol. 67, 54032p, (1967)—Abstract of Shionogi, Japanese Pat. No. 5537, 3-7-1967.
Li et al, Tet. Letters, v. 25 (20), pp. 2109–2110, (1984).

Primary Examiner—Mary Lee
Assistant Examiner—Bernard I. Dentz
Attorney, Agent, or Firm—Carroll F. Palmer

[57] ABSTRACT

This invention relates to novel guaiazulene compositions which are useful as antitumor, immunomodulatory and antifungal compositions and a process of producing guaiazulene compositions and a method for immunomodulation and inhibiting tumors and fungi utilizing guaiazulene compositions. More particularly, the compositions are derived from marine gorgorian Acalycigorgia, sp.

14 Claims, No Drawings

GUAIAZULENE DERIVATIVES AND THEIR METHODS OF USE

FIELD OF THE INVENTION

This invention relates to new organic compositions which have useful antitumor, immunomodulatory and antifungal activity. Additionally, this invention relates to newly discovered antitumor, immunomodulatory and antifungal methods of use for known and novel compositions derived from marine organisms, i.e., gorgonians Acalycigorgia sp. and their methods of use.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well known, e.g., cancer is second only to heart and vascular diseases as a cause of death in man.

While certain methods and chemical compositions have been developed which aid in inhibiting, remitting or controlling the growth of tumors further antitumor methods and chemical compositions are needed.

Immunomodulation is a developing segment of immunopharmacology. Immunomodulator compositions as the name implies, are compositions useful for modulating or regulating immunological functions in warm-blooded animals. Immunomodulators may be immunostimulants for building up immunities to or initiate healing of certain diseases and disorders or immunoinhibitors for preventing undesirable immuno reactions of the body to foreign materials. Immunomodulators have been found to be potentially useful for treating immune disease such as rheumatoid arthritis, neoplastic disease, infectious diseases, allergic reactions, autoimmune diseases, such as systemic lupus, erythematosus, and immunodeficiency diseases. Further such agents may be useful for immunotherapy of cancer or to prevent rejections in organ transplants, e.g. kidney or heart.

Various immunomodulator compositions have been discovered including muramylic acid dipeptide derivatives, levamisole, niridazole, oxysuran; flagyl, and others from the groups of interferons; interleukins; leukotrienes; and corticosteroids. Many of these compositions have been found, however, to have undesirable side effects and/or high toxicity. New immunomodulator compositions are therefore needed to provide a wider range of immunomodulator function for specific areas with a minimum of undesirable side effects.

Prevention of the growth of fungus and the infections and maladies caused by it to mammals and plants is also of importance to man. The presence of fungus may cause various diseases and infections in man including mycotic disease, e.g., pulmonary candidiasis and pulmonary blastomycosis. Certain yeastlike organisms, e.g., *Cryptococcus neoformans*, may cause serious infections of the central nervous system. More commonly known fungi infections in humans and mammals include ringworm, which are fungus infections of hair and nail areas, as well as resistant infections of the skin. Many other fungal infections inflict humans and mammals in the areas of skin, mucous membranes, intestinal tract, vaginal area and lungs.

Plants are also attacked by various fungi. Damage caused by fungus infection to agriculture amounts to billions of dollars annually. Various inorganic and organic fungistats and fungicides have been tried but with limited success. It is of course important for the fungistat or fungicide to kill the fungi but not the plant and to leave no toxic residue on the food of the plant. Various methods have been utilized to combat fungus infection in agriculture including foliage fungicide by which method plants are coated with a preventive weather-resistant fungicide. Seed treatment and soil treatment are methods which require fungicides which are safe for seeds and resist degradation by soil and soil microorganisms. Chemotherapeutants are fungicides which permeate the plant to protect new growth or eliminate infections which have already occurred within the plant. Agricultural fungistats and fungicides and their application must also meet very stringent requirements and regulations, which have been promulgated, for example, in the United States.

Considerable research and resources have been devoted to antitumor immunomodulatory and antifungal measures. While varius antitumor, immunomodulatory or antifungal agents and methods have been developed which aid in inhibiting tumors, immunomodulation and inhibiting the spread of fungus, respectively, additional methods and chemical agents are needed.

A potential source for useful organic compositions is marine plant and animal life and of particular interest are marine gorgonians. Gorgonacea are horny corals which may form fanlike or featherlike colonies of spreading branches. It has now been found that certain organic compounds derived from extracts of gorgonian Acalycigorgia sp. possess useful antitumor, immunomodulatory and antifungal acitivity.

Some compositions of interest have been previously isolated from marine gorgonian. These compositions named guaiazulene and linderazulene have been reported by Fusetani, N., Matsunaga, S., and Konosu, S. *Experientia*, 37, 680 (1981); Imre, S., Thomson, R. H., and Yalhi, B. *Experientia*, 37, 442 (1981); Li, M. K. W. and Scheuer, P. J. *Tetrahedron Letters*, 25, 587 (1984); Ibid., 25, 2109 (1984); Ibid., 25, 4707 (1984); Takeda, K., Minato, H., and Ishikawa, M., *J. Chem. Soc.*, 2591 (1965); and Takeda, K. and Nagata, W. *Chem. Pharm. Bull.*, 1, 164 (1953). These references do not disclose any antitumor, immunomodulatory or antifungal activity for these compositions. The entire disclosures of these references is hereby incorporated herein by reference. Thus, marine gorgonians and other marine life can be a source of useful raw materials for man.

SUMMARY OF THE INVENTION

It is therefore an object of the invention to provide compositions which are useful as antitumor, immunomodulatory and antifungal agents and a process for producing such compositions.

It is an additional object of the invention to provide a method for immunomodulation and inhibiting tumors and fungus growth and resultant infection and disease utilizing novel immunomodulatory, antitumor and antifungal compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described here, the invention comprises compositions of the general formula (I):

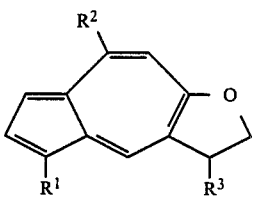

wherein $R^1$, $R^2$ and $R^3$ are the same or different and are a hydrogen or lower alkyl group. In preferred embodiments of the invention, the composition is substantially pure.

In preferred embodiment of the invention the lower alkyl groups have from 1 to 5 carbon atoms. In a more preferred embodiment of the invention $R^{1-3}$ are each methyl.

As embodied and fully described herein, the invention also comprises an antitumor, immunomodulatory or antfungal composition comprising, as active ingredient, an effective antitumor, immunomodulatory or antifungal amount, respectively, of one or more compositions of the invention and a non-toxic pharmaceutically acceptable carrier or diluent.

As embodied and fully described herein, the invention further comprises a method for inhibiting tumors comprising contacting tumor cells with an effective antitumor amount of one or more compositions of formulae I-III:

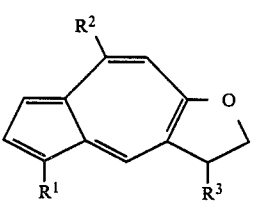

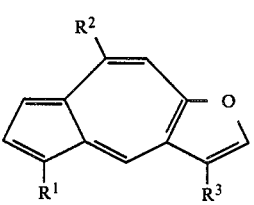

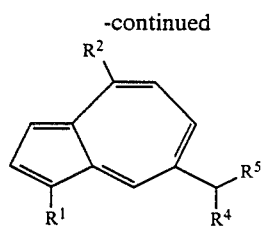

Wherein $R^{1-5}$ are the same or different and are a hydrogen or lower alkyl group.

As embodied and fully described herein, the invention further comprises a method for immunomodulation comprising utilizing an effective immunomodulatory amount of one or more compositions of formulae I-III in a site area.

As embodied and fully described herein, the invention further comprises a method for inhibiting the growth of or killing fungi comprising contacting fungi with an effective antifungal amount of one or more compositions of formulae I-III.

As embodied and fully described herein, the invention also comprises a novel process to produce compositions of forumlae I-III. The process comprises the steps of collecting marine gorgonian, Acalycigorgia, sp, contacting the marine gorgonian with a suitable organic solvent to obtain an extract; fractionating the extract; and isolating a composition of formulae I-III from the fractionated extract.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention novel compositions are provided to achieve the objects in accordance with the purposes of the invention, as embodied and fully described herein, the invention comprises compositions of the general formula I:

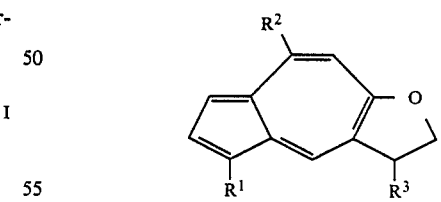

wherein $R^1$, $R^2$ and $R^3$ are the same or different and are a hydrogen or lower alkyl group.

In preferred embodiments of the invention, the composition is substantially pure.

In preferred embodiment of the invention the lower alkyl groups have from 1 to 5 carbon atoms. In a more preferred embodiment of the invention $R^{1-3}$ are each methyl.

As embodied and fully described herein, the invention also comprises an antitumor, immunomodulatory or antifungal composition comprising, as active ingredient, an effective antitumor, immunomodulatory or antifungal amount, respectively, of one or more compositions of the invention and a non-toxic pharmaceutically acceptable carrier or diluent.

As embodied and fully described herein, the invention further comprises a method fo inhibiting tumors comprising contacting tumor cells with an effective antitumor amount of one of more compositions of formulae I-III:

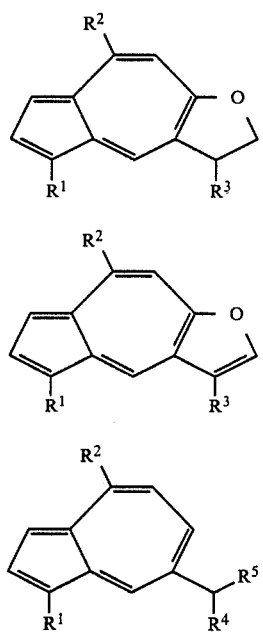

wherein $R^{1-5}$ are the same or different and are a hydrogen or a lower alkyl group.

In accordance with the invention, a method for inhibiting tumors in a host is provided comprising contacting a tumor with an effective antitumor amount of one or more compositions of formulae I-III. In accordance with the antitumor method of the invention, an effective antitumor amount of one or more of the compositions of formulae I-III may be combined with a non-toxic pharmaceutically acceptable carrier or diluent. While effective amounts may vary, as conditions in which the antitumor compositions are used vary, a minimal dosage required for activity is generally between 1 and 100 micrograms against $10^5$ tumor cells. Useful examples of non-toxic pharmaceutically acceptable carriers or diluents include, but are not limited to, the following: ethanol, dimethyl sulfoxide and glycerol.

The compositions of formulae I-III are active for inhibiting a diverse range of tumors including, but not limited to human lung, colon and mammary tumors such as lung carcinoma A549, ileocecal adenocarcinoma HCT-8, and human breast adenocarcinoma (cancer) cells MDA-MB-231. The effectiveness of the compositions of the invention for inhibiting tumors indicates their usefulness for controlling tumors in hosts including mammals and for treating cancerous cachexia.

As embodied and fully described herein, the invention further comprises a method for immunomodulation comprising utilizing an effective immunomodulatory amount of one or more compositions of formulae I-III in a warm-blooded animal (mammal) at the site of a desired immunological response, i.e. immunostimulate or immunoinhibit.

An effective amount of an immunomodulating composition of formulae I-III may be combined with a non-toxic pharmaceutically acceptable carrier or diluent. Effective amounts and concentrations of immunomodulator compositions will vary widely depending upon the intended function of the immunomodulator, the size and type of mammalian host, intended site of immunomodulation and other conditions in which the compositions of formulae I-III are used. Generally, a minimal dosage of compositions of formulae I-III which is required for immunomodulatory activity is between 5 and 50 micrograms.

In accordance with the invention, a method for inhibiting fungus in a host is provided comprising contacting fungus with an effective antifungal amount of one or more compositions of the invention. An effective antifungal amount of one or more of the compositions of formulae I-III may be combined with a non-toxic pharmaceutically acceptable carrier or diluent. While effective amounts may vary, as conditions in which the antifungal compositions are used vary, a minimal dosage required for activity is generally between 1 and 100 micrograms/ml, at an inoculum of $10^3$ fungal cells/ml, for a fungas such as, for example, *Candida albicans*. Useful examples of non-toxic pharmaceutically acceptable carriers or diluents include, but are not limited to, the following: ethanol, dimethyl sulfoxide and glycerol.

The effectiveness of the compositions of the invention for inhibiting fungus indicates their usefulness for controlling fungus and fungus related diseases in hosts including mammals. Further, the compositions of formulae I-III may be useful as agricultural fungicides.

In accordance with the invention, a process is provided to produce the compositions of formulae I-III. The process comprises the steps of collecting samples of the marine gorgonian Acalycigorgia sp., contacting the marine gorgonian with a suitable organic solvent to obtain an extract; partitioning said extract; obtaining a number of fractions from the extract; and isolating a composition of formulae I-III from the fractionated extract.

In preferred embodiments of the invention the suitable organic solvent is selected from the group of solvents consisting of acetone, ethyl acetate, methanol, toluene, chloroform, methylene chloride, methyl ethyl ketone, ethanol, methyl isobutyl ketone and mixtures thereof. Particularly preferred extracting solvents are acetone and ethyl acetate.

While those solvents listed above are the presently preferred choices for the solvents useful in accordance with the invention, other suitable solvents may be substituted. A suitable solvent system should be capable of extracting a composition of formulae I-III from other components of the gorgonian. Different ratios of solvents and any combination may be used in the solvent system of the invention as would be known to those skilled in the art.

Compositions according to the invention are prepared and/or isolated utilizing various fractionation and chromatographic techniques from the extracts obtained. Any suitable fractionation and isolation techniques as known to those skilled in the art may be utilized in accordance with the process of the invention. Suitable isolation techniques include various chromatography techniques such as reverse phase chromotography, high pressure liquid chromatography (HPLC) with suitable columns as would be known to those skilled in the art (e.g., silica gel, Lobar or ODS column) eluted with a suitable solvent such as, for example, heptane and/or ethyl acetate.

A more detailed description and explanation of a preferred embodiment of the process of the invention to produce a macrolide composition of the invention is provided in the examples section.

It is therefore apparent that the novel composition of formulae I, the process for producing the compositions of formulae I–III and the methods for utilizing the compositions of formulae I–III to inhibit tumors and fungus growth and provide immunomodulation fulfill the objects of the invention.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention. The starting materials and reagents in the examples whose methods of preparation are not indicated are commercially available from sources known to the art such as chemical supply houses.

EXAMPLES 1–3

Preparation of:

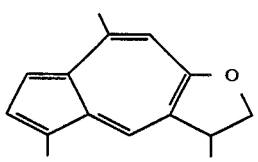

Composition 1

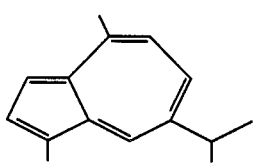

Composition 2

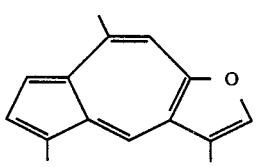

Composition 3

The gorgonian Acalycigorgia sp. (600 g), was collected at Cape Zampa, Okinawa. The collected gorgonian was extracted by steeping in acetone (3 L). The acetone extract was concentrated, and the resulting aqueous suspension was extracted with ethyl acetate to give 3.4 gms of an oil. A part of the oil (2.7 gms) was chromatographed on a silica gel column by eluting with a mixture of heptane and ethyl acetate (10:1) into two portions. The first portion (1.02 g) containing blue pigments was placed on a bed of reverse phase adsorbent (RP-8) and successively eluted with methanol and acetone. The same filtration was repeated again with the methanol eluate to give 320 mg of a mixture containing blue pigments. Separation of the mixture on a Lobar Si-60 column (heptane-ethyl acetate 19:1) gave five fractions. Each of the three pigment-containing fractions was first separated by preparative TLC on silica gel (heptane-ethyl acetate 30:1 to 10:1) and then purified by HPLC on a Hibar Si-60 column (heptane-ethyl acetate 40:1 to 20:1) to give 47 mg of dihydrolinderazulene (1) as an oil, $[\alpha]_D$ +800° (c 0.05, $CHCl_3$), 93 mg of guaiazulene (2) as an oil, and 7.8 mg of linderazulene (3) as a crystalline solid, mp 105.5° C.

The compositions 2 and 3 were identified by comparison of their spectral data with those earlier reported for the compositions (See e.g. Li, M. K. W.; Scheuer, P. S.; Tetrahedron Letters, 25, No. 6, pp. 587–590 (1984) for (2) and Imre, S.; Thomson, R. H.; Yalhi, B.; Experentia, 37, 442–443 (1981) for (3)). The structure of dihydrolinderazulene (1) was determined by the following spectral data: HREIMS m/z 212.1202 (calcd for $C_{15}H_{16}O$ 212.1201); LREIMS m/z 212 (M+, 100), 197 (60), 182 (22), 169 (19), 165 (9), 154 (11), 153 (11), 141 (8), 128 (8), 115 (8), and 106 (6 rel%); 1H NMR (acetone-$d_6$) δ8.10 (1H, s), 7.26 (1H, d, J=3.8 Hz), 7.15 (1H, d, J=3.8 Hz), 6.69 (1H, s), 4.69 (1H, dd, J=8.8, 8.8 Hz), 4.14 (1H, dd, J=8.8, 6.6 Hz), 3.72 (1H, m), 2.73 (3H, s), 2.57 (3H, s), and 1.40 (3H, d, J=6.8 Hz); $^{13}$C NMR (acetone-$d_6$) δ166.23 (s), 146.14 (s), 134.16 (s), 132.68 (s), 131.97 (d), 129.54 (d), 126.75 (s), 124.47 (s) 115.74 (d), 109.53 (d), 77.93 (t), 39.96 (d), 24.40 (q), 20.68 (q), and 12.83 (q). The structure of 1 was confirmed by dehydrogenation over Pd/C which gave rise to a sample identical with linderazulene (3).

ANTITUMOR ACTIVITIES OF THE COMPOUNDS OF THE INVENTION

The following assay method was utilized to illustrate the antitumor effectiveness of the compositions of Formulae I–III corresponding to compositions 1–3 of the examples.

P388 MOUSE LEUKEMIA CELL ASSAY

Maintenance of Cell Line

P388 mouse leukemia cells are grown in Dulbecco MEM medium with 10% horse serum 4 mM, glutamine, and 20 μg/ml gentamycin (Biologos, Inc.). Cells are incubated in 10% $CO_2$ and subcultured 2 times per week.

PROCEDURE

1. Add composition to each well of a 24-well plate or tube and allow solvent to evaporate to dryness.
2. Add 2 ml (1.2×10$^5$) cells to each well or tube and mix.
3. Incubate in 10% $CO_2$ at 37° for 48 hours.
4. Read plates with an inverted microscope, scoring activity from 1+ to 4+ as follows: ND (not detectable), >90%, 1+, 75–90%; 2+, 50–74%; 3+, 25–49%; 4+, <25% of control growth. Alternatively, scoring may be expressed as IC$_{50}$ which represents the minimum concentration of the composition required to inhibit 50% of the cell growth on the plate. Cell counts are performed on each tube and results are reported as percent of control.

HUMAN TUMOR CELL LINE ASSAY

Maintenance of Cell Line

HCT-8 human colon tumor cells are growth in ROM1 1640 medium (GIBCO). A549 human lung carcinoma cells are cultured in Dulbecco medium (Biologos, Inc.). All media are supplemented with 10% fetal bovine serum and contain 50 µg/ml gentamycin. All human tumor cell lines are incubated at 5% $CO_2$ at 37° and subcultured once a week.

PROCEDURE

1. Seed 1 ml cell (5000 HCT-8, 8000 A549, 12000 MCF-7) in each well of a 24-well plate.
2. Incubate in a $CO_2$-incubator for 48 hours.
3. Add composition to each well and incubate for an additional 120 hours.
4. Discard medium and stain with methylene blue (HCT-8) or crystal violet (A549 and MCF-7).
5. Compare cell density of drug-treated well with that of the control (no drug added) as follows: ND (not detectable), >90%; 1+, 75-90%; 2+, 50-74%; 3+, 25-49%, 4+, >25% of control growth.

Positive control—Vinblastine or Vincristine in aqueous solution.

Final Conc. of Vinblastine or Vincristine control (use 2 µl/assay)

| Solution Conc. | Amt added | Final conc. in test |
|---|---|---|
| 5 mg/ml | 2 ul | 5 ug/ml |
| 1 mg/ml | 2 ul | 1 ug/ml |
| 0.1 mg/ml | 2 ul | 0.1 ug/ml |
| 0.05 mg/ml | 2 ul | 0.05 ug/ml |

Assays with human breast adenocarcinoma cells, MDA-MB-231 are carried out in substantial accordance with the above procedures.

MIXED LYMPHOCYTE REACTION (MLR) ASSAY

The assay method was uded to identify immune response modifiers of the compositions of Formulae I-III corresponding to composition 1-3 of the samples.

Murine Lymphocyte Preparation

Aseptically removed spleens from BALB/c and C57BL/6 mice were homogenized, separately, in RPMI 1640 medium with 10% fetal calf serum, 2% L-glutamine, 15 mM HEPES, 1% antibiotic-antimycotic solution and 25 µg/ml gentamycin (GIBCO). Lymphocytes were then derived by differential cetrifugation after red blood cell lysing and serial cell washing in complete media. Cells were adjusted to equal concentrations ($2.5 \times 10^6$ cells/ml) and combined after removal of negative control aliquots. Incubation conditions for the cells were 5% $CO_2$, 95% air at 37° C.

PROCEDURE

1. Add composition to each well of a 96-well plate and allow solvent to evaporate to dryness, if not aqueous.
2. Add 0.2 ml mixed lymphocytes (BALB/c+C57BL/6) to each well and mix.
3. Incubate in 5% $CO_2$ at 37° C. for 86 hours.
4. Pulse wells with 0.1 ml $^3$H-thymidine (1 uCi/well).
5. Incubate in 5% $CO_2$ at 37° C. for 6 hours.
6. Harvest plates and add 2 ml scintillant to each vial containing a filter disc.
7. Count vials in a liquid scintillation counter (Beckman).
8. Average replicate counts and report data as percent of positive control. The criteria for immunostimulatory effectiveness is a value of 150%, or greater, above control values for mixed lymphocytes in culture.

ANTIFUNGAL ACTIVITIES OF THE COMPOSITIONS OF THE INVENTION

The following assay method was utilized to demonstrate the in vitro antifungal effectiveness of the compositions of Formulae I-III, to compositions 1-3 of the examples of the invention as reported in Table 3.

Preparation of inocula

Candida albicans: *C. albicans* (Ca) is grown on Sabouraud dextrose agar to produce single colonies one of which is used to inoculate Sabouraud dextrose broth. The broth is incubated at 37° C. with shaking at 200 rpm for 18 hrs., the resultant culture is frozen with 10% (v/v) glycerol at −80° C. and used as the inoculum for the anti-Candida assay.

Assay protocols

1. Disc diffusion assay

*C. albicans* is inoculated into melted Sabouraud dextrose agar at 45° C. to give a cell density of approximately 1000 cells/mL. Plates are prepared with 10 mL of the seeded agar in a 10 cm×10 cm petri dish. These plates are stored at 4° C. until needed for the assay.

Paper discs (6.35 mm) are impregnated with the test substance and allowed to dry. They are then placed onto the surface of a test plate prepared as detailed above. Plates are incubated overnight at 37° C. after which time the zones of growth inhibition can be read, these are expressed as the diameter of the zone in millimeters.

2. Minimum inhibitory concentration (MIC)

Two-fold dilutions of the drug are prepared in 50 µL volumes of Sabouraud dextrose broth using 96-well microtiter plates. An inoculum of *C. albicans* is added in a small volume to give a cell density of approximately 1000 cells/mL. Plates are incubated at 37° C. overnight. 10 uL of Triphenyl tetrazolium chloride (1% w/v) is then added to each well; a further 2 hour incubation results in a deep coloration of the microorganism. The MIC is the lowest concentration of the drug which has completely inhibited growth.

The results of the above assays are summarized in Table 3.

TABLE 1

| | Antitumor activity | | | | |
|---|---|---|---|---|---|
| Composition | P388 IC$_{50}$ (ug/ml) | Dose (ug/ml) | HCT-8 | A549 | MDA-MB-231 |
| (1) Dihydrolinderazulene | 35 | 50 | 4+ | 4+ | 4+ |
| | | 10 | 2+ | 2+ | 4+ |
| | | 5 | ND | ND | 3+ |
| | | 1 | NT | NT | ND |
| (2) Guaiazulene | 35 | 50 | 4+ | 4+ | 4+ |
| | | | ND | ND | ND |
| (3) Linderazulene | 50 | 50 | 4+ | 4+ | 4+ |
| | | 10 | 1+ | 2+ | 1+ |
| | | 5 | ND | 1+ | 1+ |
| | | 1 | NT | ND | ND |

TABLE 2

| Immunomodulatory activity | | |
|---|---|---|
| | Dose (ug/ml) | % Reference |
| Composition (1) | 50 | 1 |
| | 5 | 255 |
| Composition (2) | 50 | 351 |
| | 5 | 284 |
| Composition (3) | 50 | 19 |

TABLE 2-continued

| Immunomodulatory activity | |
|---|---|
| Dose (ug/ml) | % Reference |
| 5 | 155 |

TABLE 3

| Antifungal activity | |
|---|---|
| | C. albicans MIC (ug/ml) |
| Composition (1) | 50 |
| Composition (2) | 25 |
| Composition (3) | 12.5 |

The data provided in Tables 1-3 reports the in vitro effectiveness of the compositions of formulae I-III as antitumor, immunomodulator and antifungal agents. These results indicate that these Compositions are effective for inhibiting tumors and fungus growth or regulating immune responses in vitro in hosts including warm-blooded animals or mammalian hosts.

The scope of the present invention is not limited by the description, examples, and suggested uses herein and modifications can be made without departing from the spirit of the invention. The present invention contemplates derivatives of the compositions of formula I as modifications of the present invention and within the scope of the invention. For example, it may be noted that other derivatives of the composition of example 1 such as halogen or sulfonyl substituted derivatives of composition 1 may be prepared that may possess antitumor, immunomodulatory or antifungal activity analogous to those preferred embodiments described above. Further, the compositions described herein may have other useful applications such as, for example, analgesic applications or as starting materials for the preparations of other compositions. Therapeutic application of the compositions of the present invention can be accomplished by any suitable therapeutic method and technique as is presently or prospectively known to those skilled in the art. Thus, it is intended that the present invention cover the modifications and variations of this invention provided that they come within the scope of the appended claims and their equivalents.

What is claimed is:

1. A substantially pure compound according to the formula:

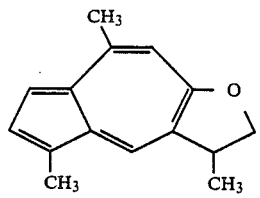

2. A substantially pure compound according to the formula:

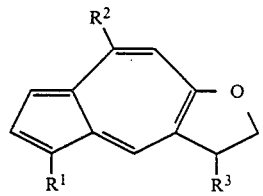

wherein $R^1$, $R^2$ and $R^3$ are the same or different and are hydrogen or lower alkyl.

3. A compound of claim 2 wherein the lower alkyl group has from 1 to 5 carbon atoms.

4. An immunomodulatory composition comprising, as active ingredient, an effective immunomodulatory amount of one or more of the compounds of claim 2 and a non-toxic pharmaceutically acceptable carrier or diluent.

5. An immunomodulatory composition comprising, as active ingredient, an effective immunomodulatory amount of the compound of claim 1 and a non-toxic pharmaceutically acceptable carrier or diluent.

6. An antifungal composition comprising, as active ingredient, an effective antifungal amount of one or more of the compounds of claim 2 and a non-toxic pharmaceutically acceptable carrier or diluent.

7. An antifungal composition comprising, as active ingredient, an effective antifungal amount of the compound of claim 1 and a non-toxic pharmaceutically acceptable carrier or diluent.

8. A method of immunomodulation comprising applying to an immune modulation site an effective immunomodulatory amount of one or more compounds of claim 2.

9. A method of immunomodulation comprising applying to an immune modulation site an effective immunomodulatory amount of the compound of claim 1.

10. A method of inhibiting fungus growth in a host comprising contacting fungus with an effective antifungal amount of one or more compounds of claim 2.

11. A method of inhibiting fungus growth in a host comprising contacting fungus with an effective antifungal amount of the compound of claim 1.

12. A process to produce the compound of claim 1 comprising the steps of:
providing a quantity of marine gorgonian Acalycigorgia, sp.;
contacting said gorgonian with a suitable organic solvent;
obtaining a solvent extract from said gorgonian;
fractionating said extract; and
isolating the compound of claim 1 from the fractionated extract.

13. A therapeutic method for treating cancerous cachexia caused by the presence of a tumor in a host comprising administering to said host, without treating the tumor per se, an effective amount of a compound of claim 2.

14. A therapeutic method for treating cancerous cachexia caused by the presence of a tumor in a host comprising administering to said host, without treating the tumor per se, an effective amount of the compound of claim 1.

* * * * *